(12) United States Patent
Chaussard et al.

(10) Patent No.: US 12,268,792 B2
(45) Date of Patent: Apr. 8, 2025

(54) SYSTEM FOR CLEANING AND/OR DISINFECTING A HOLLOW TUBE, IN PARTICULAR A DOOR HANDLE LEVER

(71) Applicant: CÉCLEAN, Compiegne (FR)

(72) Inventors: Philippe Chaussard, Compiegne (FR); Aurélien Vauquelin, Compiegne (FR)

(73) Assignee: CÉCLEAN, Compiegne (FR)

( * ) Notice: Subject to any disclaimer, the term of this patent is extended or adjusted under 35 U.S.C. 154(b) by 918 days.

(21) Appl. No.: 17/428,346

(22) PCT Filed: Feb. 7, 2020

(86) PCT No.: PCT/FR2020/000026
§ 371 (c)(1),
(2) Date: Aug. 4, 2021

(87) PCT Pub. No.: WO2020/161402
PCT Pub. Date: Aug. 13, 2020

(65) Prior Publication Data
US 2022/0118141 A1    Apr. 21, 2022

(30) Foreign Application Priority Data

Feb. 8, 2019 (FR) .................................... 1901282

(51) Int. Cl.
*A61L 2/18* (2006.01)
*A61L 2/24* (2006.01)
*E05B 1/00* (2006.01)

(52) U.S. Cl.
CPC ...... *A61L 2/18* (2013.01); *A61L 2/24* (2013.01); *E05B 1/0069* (2013.01); *A61L 2202/14* (2013.01); *A61L 2202/17* (2013.01)

(58) Field of Classification Search
CPC ...... E05B 1/0069; E05B 47/0012; A61L 2/18; A61L 2/24; A61L 2202/14; A61L 2202/17; B08B 9/023; B62B 5/069
See application file for complete search history.

(56) References Cited

U.S. PATENT DOCUMENTS

2006/0267299 A1 * 11/2006 Dunser ................... B08B 9/023
280/33.992
2009/0188311 A1 * 7/2009 Cadieux ............ A61M 5/14546
73/149

(Continued)

FOREIGN PATENT DOCUMENTS

DE     102008047556 B3    1/2010
JP     H04271884 A    9/1992

OTHER PUBLICATIONS

International Search Report and English translation for corresponding International Application No. PCT/FR2020/000026, dated May 19, 2020. 5 pages.

*Primary Examiner* — Jennifer Wecker
*Assistant Examiner* — Brady C Pilsbury
(74) *Attorney, Agent, or Firm* — Leason Ellis LLP

(57) ABSTRACT

The present invention relates to a system (8) for cleaning and/or disinfecting a hollow tube (4), comprising: —The hollow tube (4), —a ring (18) mounted so as to slide over the hollow tube (4), the ring (18) enclosing an absorbent pad impregnated with a disinfecting and/or degreasing liquid, and arranged around the hollow tube (4). The system (8) further comprises an electromechanical actuation device (20) for actuating the ring arranged inside the hollow tube, the device being a motorised linear potentiometer and comprising a longitudinal translational drive element (26). Moreover, a longitudinal slot (11) is provided in the hollow tube (4), the element (26) protruding through the longitudinal slot (11) and being mechanically connected to the ring (Continued)

(18), in order to move the ring (18) in longitudinal translation along the hollow tube (4). The hollow tube (4) can be a lever for operating a door handle (2), or indeed a tube of a bar equipping a transport means, a T-bar door pull handle or a ramp.

13 Claims, 10 Drawing Sheets

(56) References Cited

U.S. PATENT DOCUMENTS

2009/0193607 A1\* 8/2009 Adell .................. A61L 2/10
  15/246
2023/0212877 A1\* 7/2023 Horvath .............. H02K 7/1853
  15/4

\* cited by examiner

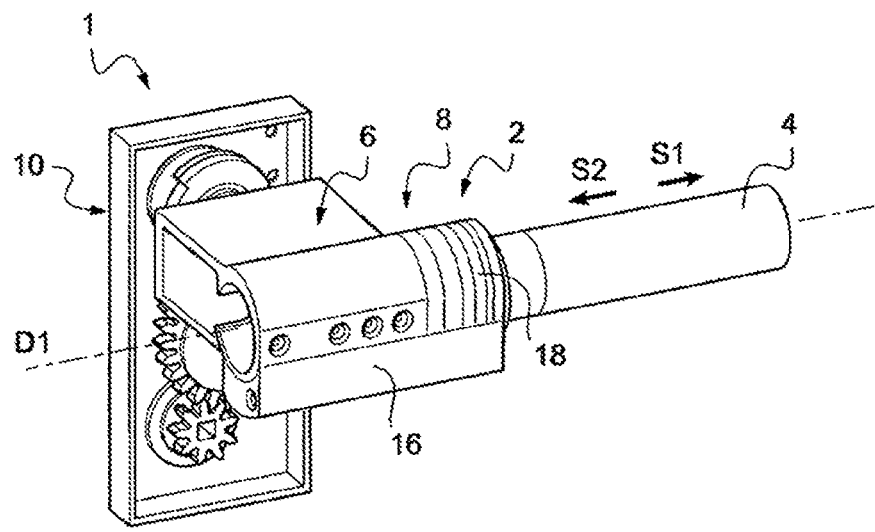
[Fig. 1]
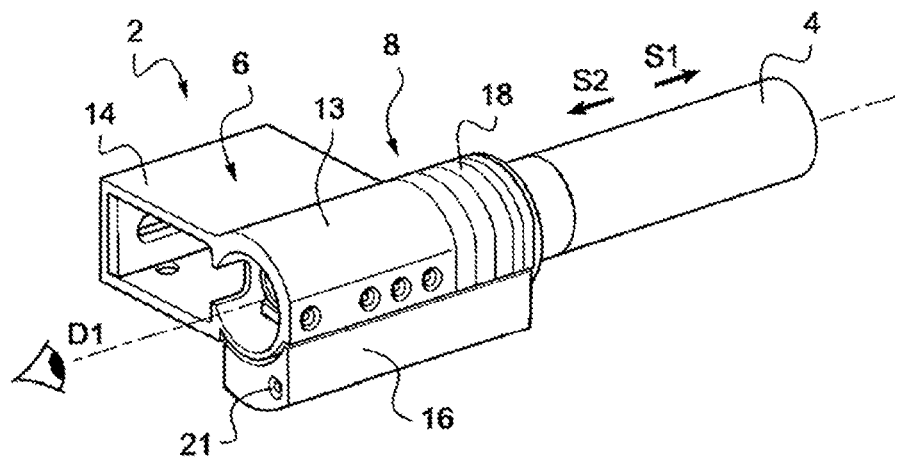
[Fig. 2]

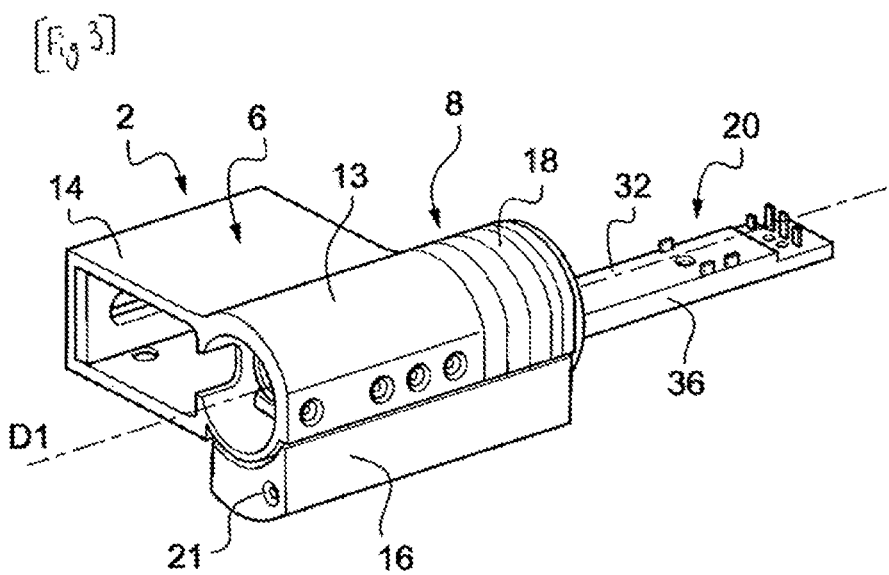
[Fig. 3]
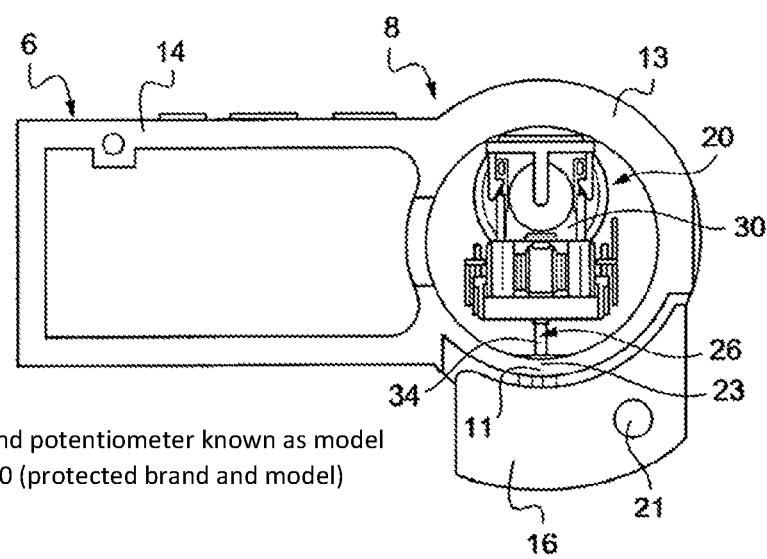
[Fig. 4]
AlpS® brand potentiometer known as model
401840 (protected brand and model)

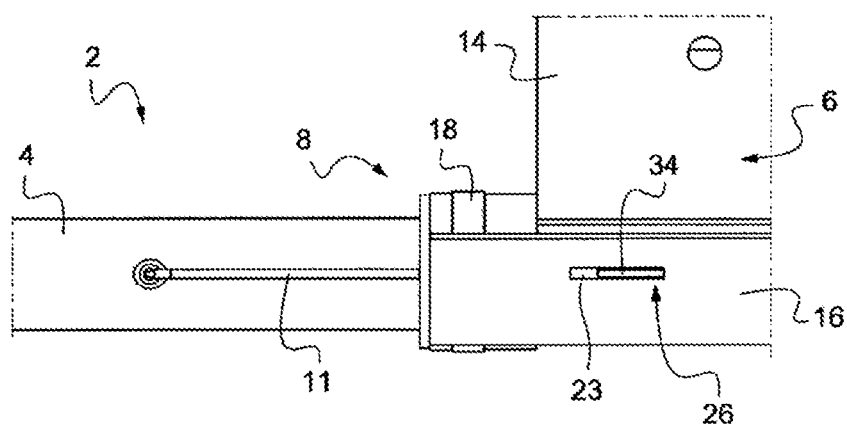
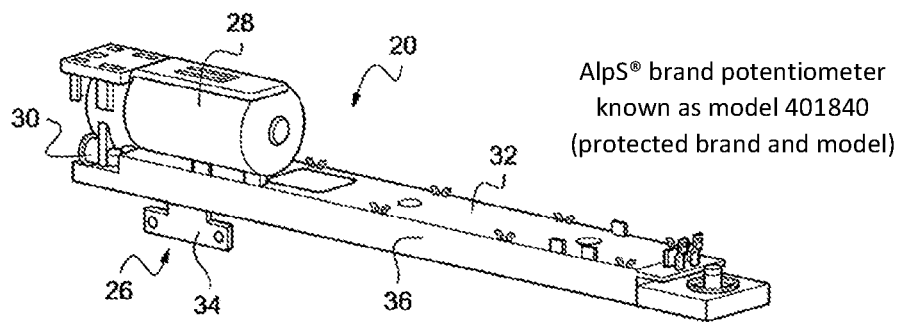
AlpS® brand potentiometer known as model 401840 (protected brand and model)

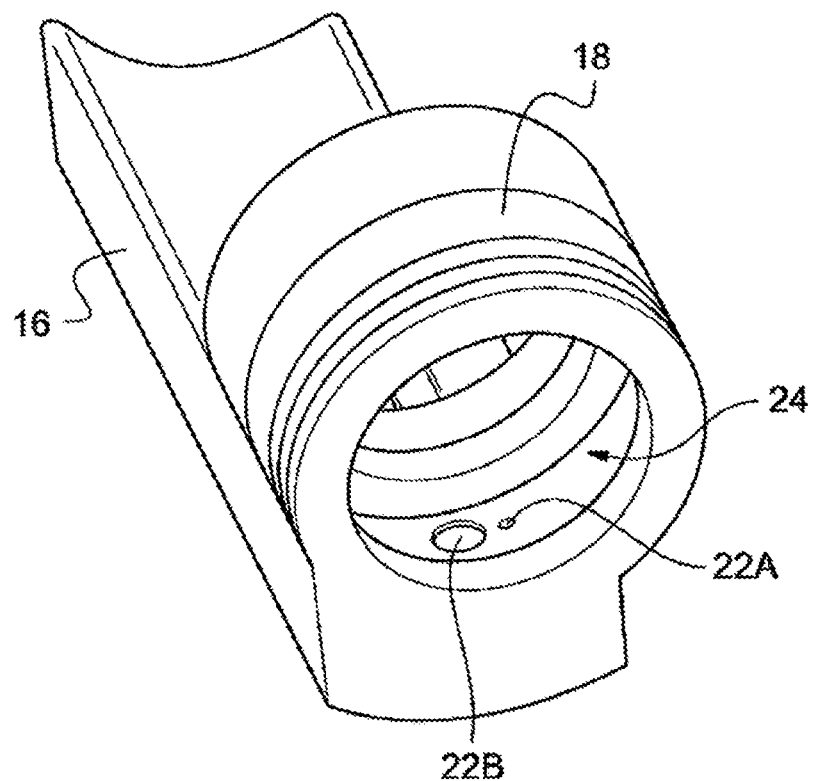
[Fig. 7]
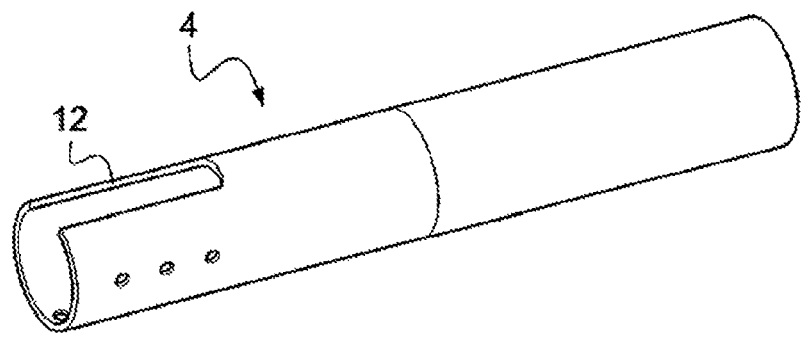
[Fig. 8]

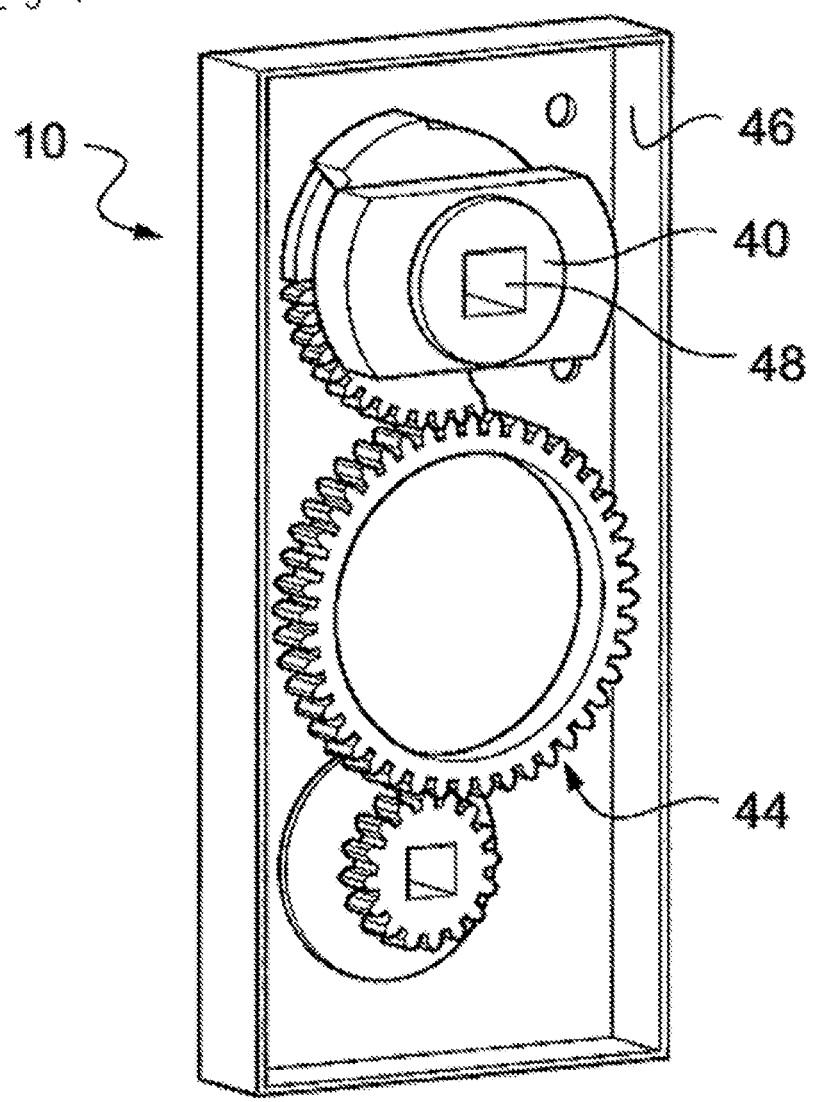

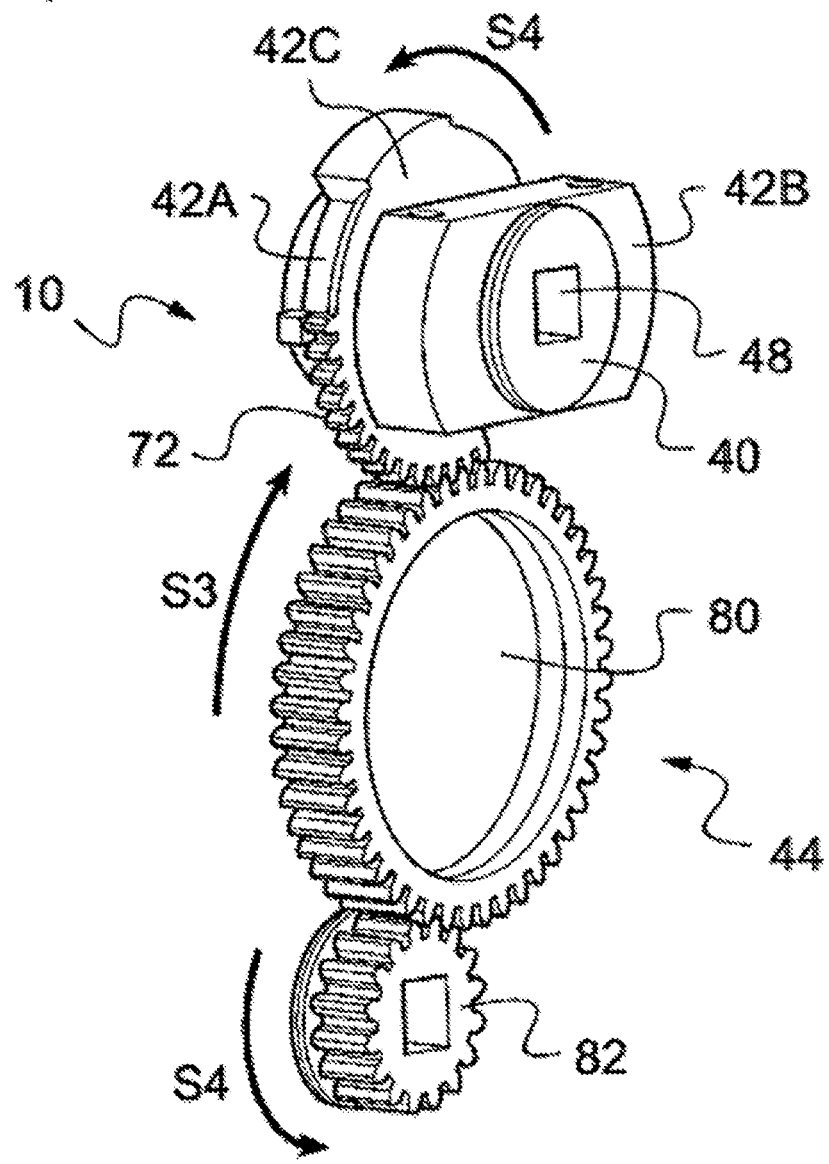

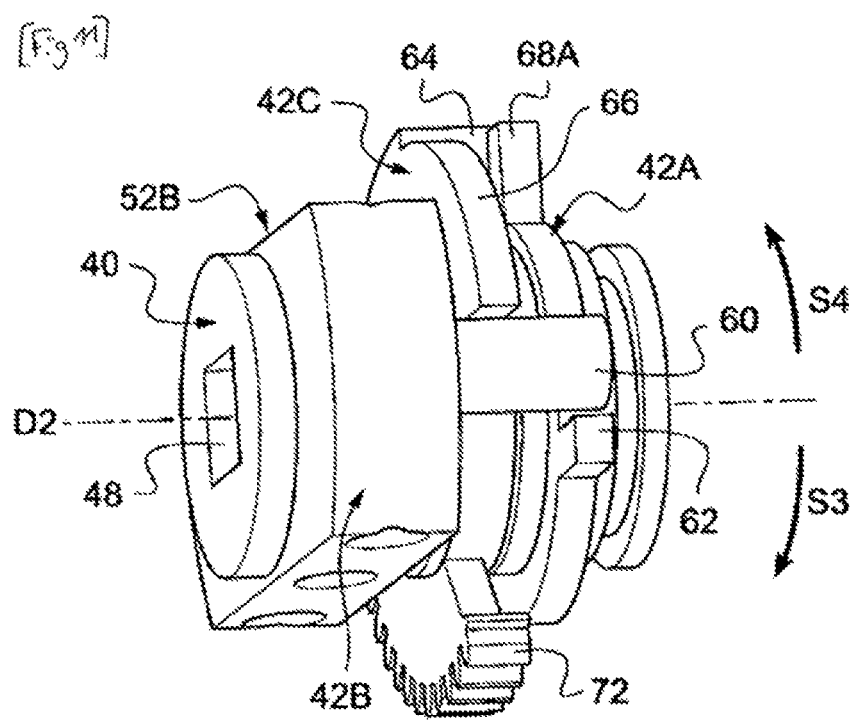

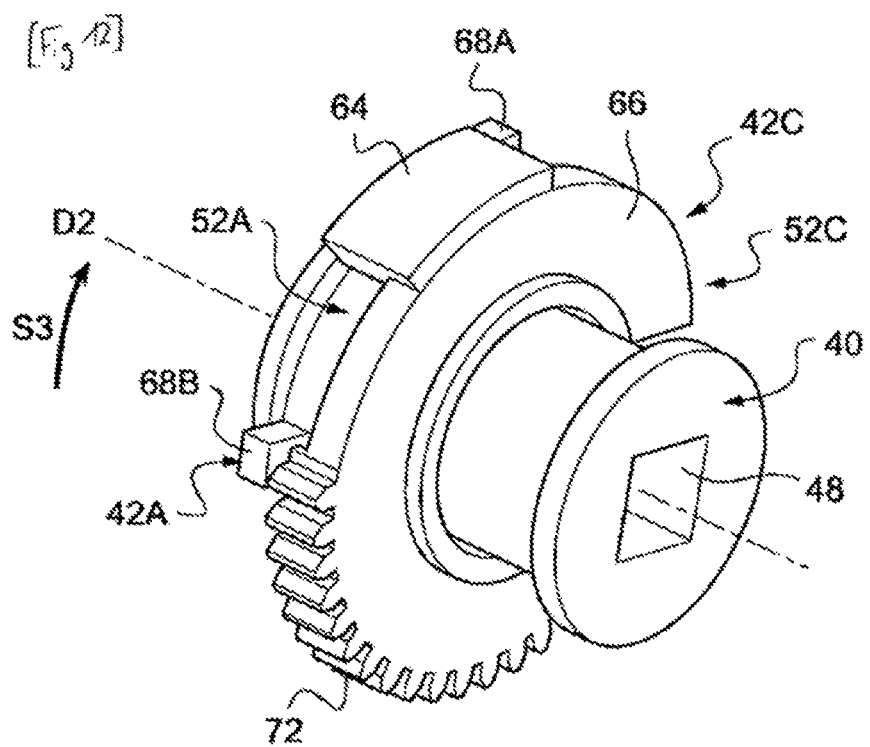
[Fig. 12]
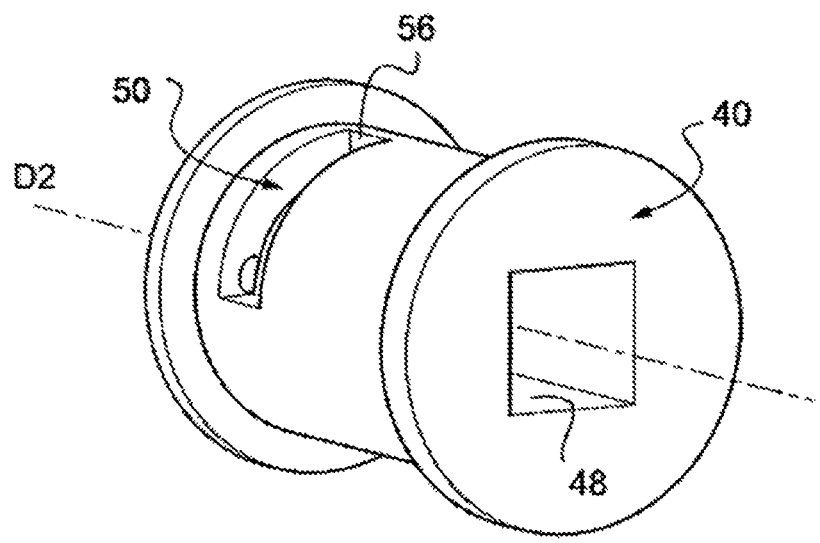
[Fig. 13]

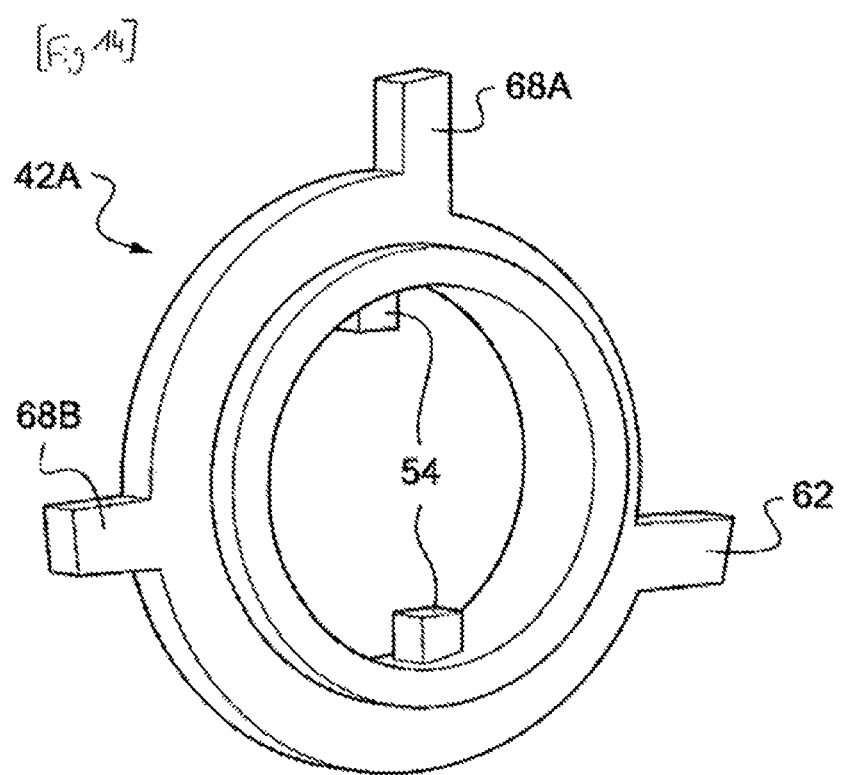

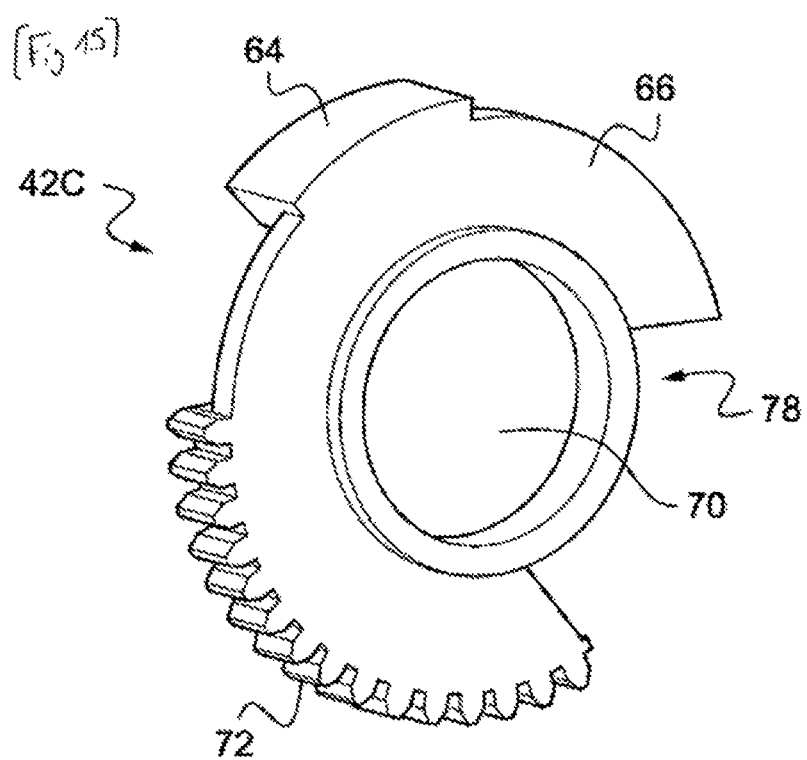
[Fig. 15]
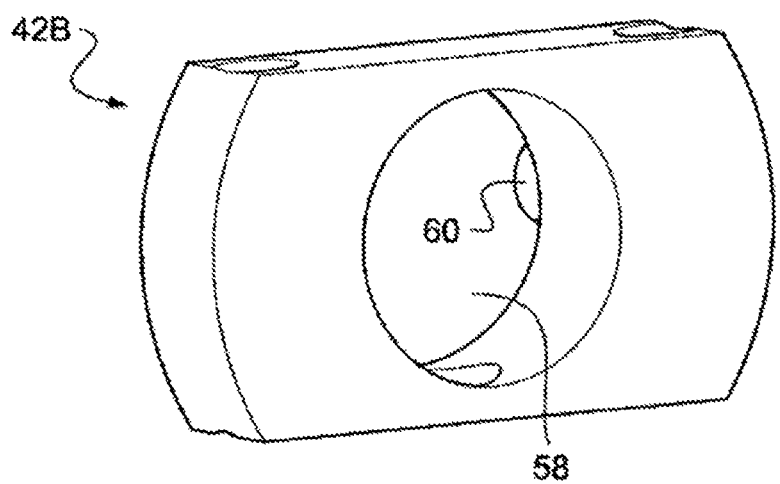
[Fig. 16]

SYSTEM FOR CLEANING AND/OR DISINFECTING A HOLLOW TUBE, IN PARTICULAR A DOOR HANDLE LEVER

CROSS-REFERENCE TO RELATED PATENT APPLICATIONS

This application is a U.S. National Stage Application under 35 U.S.C. § 371 of International Patent Application No. PCT/FR2020/000026 filed Feb. 7, 2020, which claims the benefit of priority of French Patent Application No. 1901282 filed Feb. 8, 2019, both of which are incorporated by reference in their entireties. The International Application was published on Aug. 13, 2020, as International Publication No. WO 2020/161402 A1.

TECHNICAL FIELD

The present invention relates to an automated cleaning and/or disinfection system for a hollow tube, which can in particular be a door handle lever, or a tube of a bar equipping a transportation means, a marshal's baton type handle or a handrail such as a stairway handrail for example. The invention is applicable in particular, without this being exclusive or limiting, to the field of degreasing and bactericidal door handle cleaning systems for use particularly in establishments receiving the public.

The invention also relates to an assembly including a system of this type and at least one door handle equipped with a handle operating lever and with a lever support.

PRIOR ART

In establishments receiving the public, there is a need to be able to guarantee that the opening of any door in the establishment can be accomplished by means of a handle that ensures the absence of microbial germs and organic matter on it. In fact, the contact of a hand with the operating lever of a door handle is of such a nature as to constitute a risk of transmitting infectious germs or pathogenic agents. This is particularly critical in hospitals, for example, or even in toilets installed in public places.

More generally, there is a need to be able to guarantee a cleaning, without transmission of infectious germs or pathogenic agents, of any hollow tube such as a door handle lever, a tube of a bar equipping a transportation means such as a bus or subway, a marshal's baton type handle or a handrail such as for example a stairway handrail.

A first known solution consists of having a user move, by longitudinal translation on the hollow tube, a cleaning and/or disinfection device. However, a manual contact of this type between the hand of the user and the device causes transfers of bacterial and/or microbial strains on the hollow tube, even if the tube has been cleaned and/or disinfected by the device.

In order to correct the aforementioned disadvantage and totally eliminate the risks of microbial or infectious transmission, automated cleaning and/or disinfection systems are known for a hollow tube, which can for example be a door handle lever. Such systems allow the handle to be degreased and/or disinfected after each use. A system of this type is described, for example, in patent document GB 2433 878 A. The system comprises, besides the operating lever, a reservoir of a disinfectant and degreasing liquid; a ring integral with the reservoir and mounted so as to slide on the lever; and a system for actuating the ring. The ring encloses an absorbent pad in fluid communication with the reservoir, said pad being arranged around the lever. The ring, which includes elements of magnetic material, is set in motion along the lever by magnetic coupling with a coil, said coil forming a first portion of the actuation system. The coil is arranged inside the lever, which itself is propelled by air from a piston-cylinder assembly, said assembly forming the second portion of the actuation system. This piston-cylinder assembly is mechanically connected to the door, so that the movement of the door controls the actuation of the ring in one direction or in another along the lever.

However, a first disadvantage of the system proposed in patent document GB 2 433 878 A, in which the ring is driven by a magnetic field, is that it generates radial forces which accentuate the friction of the ring on the lever. This has the consequence that the cleaning obtained by a system of this type is repeatable only with difficulty. In addition, due to the fact that the system is an open loop, no monitoring or regulation of the movement is carried out. Thus, the speed of the movement is not monitored by the system. However, due to the relatively high speeds attained by the coil driven by an elevated or reduced air pressure, this results in a poor application of the liquid by a pad that is too rapid in its movement. Finally, a system of this type is very bulky, does not guarantee that the movement of the ring has actually occurred over the entire length of the lever, and requires a user to be able to obtain a special door that is compatible with the system.

Patent document DE 10 2008 047556 83 describes a cleaning and/or disinfection system of a door handle lever. The system comprises, in addition to the lever, a ring mounted so as to slide on the lever and an electromechanical actuating device of the ring arranged inside the lever. The ring encloses an absorbent pad impregnated with a disinfecting and/or degreasing liquid, the absorbent pad being arranged around the lever. The electromechanical actuating device, in the form of a threaded spindle coupled to a motor, includes an element for driving the ring in longitudinal translation in the form of a screw nut arranged on the spindle. A longitudinal slot is arranged in the lever. The longitudinal translation element protrudes through the longitudinal slot and is mechanically connected to the ring, in order to move the ring in longitudinal translation along the lever.

However, one disadvantage of the system proposed in patent document DE 10 2008 047556 B3 is that it does not allow precise monitoring of the position of the ring on the hollow tube formed by the lever. Consequently, due to this lack of monitoring and of identification of the position of the ring by the system, the system does not guarantee that the movement of the ring has in fact occurred over the entire length of the tube. This is detrimental to the effectiveness of the cleaning and/or the disinfection of the tube. Another disadvantage of this system is that it is relatively fragile. In fact, if a user of the system (such as a child, for example) happens to pull on the ring, the coupling between the ring and the threaded spindle can alter the shank or the motor if the ring is pulled too energetically. Finally, the noise generated by the operation of the threaded spindle makes such a system poorly compatible with the public places in which it must be installed.

SUMMARY OF THE INVENTION

The invention therefore has as its goal an automated cleaning and/or disinfection system for a hollow tube that is reliable, discreet and compact, and makes it possible to obtain repeatable cleaning over the entire length of the tube, over a given distance and in a given time.

Another goal of the invention is to supply an automated cleaning and/or disinfection system for a hollow tube which allows precise monitoring of the position of the ring on the hollow tube.

Another goal of the invention is to supply in particular an automated cleaning and/or disinfection system for a door handle lever which does not necessitate changing or modifying the door, or the mortise of the door.

To this end, according to a first aspect of the invention, the invention relates to a cleaning and/or disinfection system for a hollow tube, comprising
- the hollow tube;
- a ring mounted so as to slide on the hollow tube, the ring enclosing an absorbent pad impregnated with a disinfecting and/or degreasing liquid, the absorbing pad being arranged around the hollow tube;
- an electromechanical actuating device for the ring arranged inside the hollow tube, said device including a longitudinal translation drive element;
- a longitudinal slot is provided in the hollow tube, the longitudinal translation drive element protruding through said longitudinal slot and being mechanically connected to the ring, in order to move the ring in longitudinal translation along the hollow tube;

wherein the electromechanical actuating element is a motorized linear potentiometer.

Due to the electromechanical actuating device of the ring arranged inside the hollow tube, the cleaning and/or disinfection system according to the invention is particularly compact. In addition, such electromechanical actuation of an element, driving the ring in longitudinal translation along the tube, allows reliable and repeatable cleaning to be obtained. The system according to the invention thus makes it possible to guarantee that the contact between the user's hand and the hollow tube, at any time and at any location on it, is always clean and disinfected. Moreover, due to the potentiometric feedback obtained from the potentiometer, the system according to the invention makes it possible to guarantee that the movement of the ring, and therefore the cleaning of the hollow tube, has actually occurred over the entire length of the tube. In fact, a motorized linear potentiometer of this type allows the system to obtain a voltage value proportional to the position of the ring. This position of the ring can therefore be determined by the system at any time, in a more accurate manner. This advantageously makes it possible to improve the monitoring of the position of the ring on the tube compared to the known devices of the prior art, thus allowing the effectiveness of the cleaning and/or of the disinfection to be improved by ensuring that all the portions of the tube are in contact with the pad. In addition, the use of a motorized linear potentiometer of this type makes it possible to obtain a reliable and discreet cleaning and/or disinfecting system.

In addition, in the particular case where the tube is an operating lever of a door handle, the user of the cleaning and/or disinfecting system according to the invention has no need to obtain a special door in order to use the system. For a use of this type, it is only necessary to replace a conventional door handle with a door handle equipped with the system according to the invention. It is in no way necessary to change or modify the door, nor widen the mortise of the latter, unlike certain automated cleaning and/or disinfecting systems of the prior art. A conventional mortise lock is also advantageously compatible with a handle equipped with the system according to the invention.

Particular forms of the cleaning and/or disinfection system are defined according to the invention.

Advantageously, the electromechanical actuation system also includes a motor fed with electrical power and a pulley/belt assembly actuated by the motor, the longitudinal translation drive element being connected to the pulley/belt assembly. A pulley/belt assembly of this type allows high movement speeds to be attained, while being mechanically reversible and causing reduced noise. This mechanical reversibility of the system is particularly advantageous within the scope of the present invention, for reasons of safety but also to allow a user to be able to a manually move the ring, for example for maintenance.

Advantageously, the longitudinal translation element is a movable carriage mounted in translation on a fixed portion of the motorized linear potentiometer and including a tab, and a longitudinal slot is provided in the ring, the tab protruding through the respective longitudinal slots of the hollow tube and the ring.

Advantageously, the hollow tube or the ring is equipped with at least one visual marking, particularly at least one colored marking or at least one engraved locator, said at least one visual marking being indicative of a liquid and/or electrical power breakdown. This allows a user to be reliably informed regarding a liquid and/or electrical power breakdown of the system, so that the user can then recharge the liquid disinfectant and/or degreaser, and/or replace the power supply batteries.

Advantageously, the electromechanical actuating device also comprises a motor control microcontroller, connected to the motor. This makes it possible to ensure electronic regulation of the motor, which makes it possible to guarantee repeatable and constant behavior of the latter, and therefore reliable, constant and repeatable cleaning of the hollow tube. In addition, electronic regulation of this type guarantees good application of the liquid on the tube by the absorbent pad.

According to a particular exemplary embodiment of the invention, the hollow tube is an operating lever of a door handle.

Advantageously, the electromechanical actuating device also includes an inclinometer connected to the microcontroller, said inclinometer being configured to detect a movement of the lever and to transmit to the microcontroller a corresponding detection signal, the microcontroller being configured to transmit to the motor, after a predefined period of time has elapsed since the reception of the detection signal, a signal controlling a back-and-forth movement of the ring along the lever. This makes it possible to obtain a reliable and entirely automated cleaning of the lever, without disturbing the user during the manipulation of the handle for opening or closing the door. The predefined duration is in fact determined beforehand via experimental use tests. A duration of between one second and three seconds can, for example, prove to be adequate. According to one particular technical feature of the invention, the microcontroller comprises processing means and memory means storing a source code, the source code including program instructions which, when executed by the processing means, trigger a control sequence of the motor in order to move the ring in longitudinal translation along the hollow tube.

Advantageously, the microcontroller also comprises a pre-calibrated counter, the counter recording a predetermined number of cycles of the system, corresponding to a liquid and/or electrical power supply breakdown, and the control sequence of the motor is configured within the source code so that, when the counter has reached the predetermined number of cycles, the microcontroller commands the motor to bring the ring, at the end of its movement, into a predefined position on the hollow tube allowing the visual marking to appear. The predetermined number of cycles is, for example, determined by prior calibration studies, and corresponds to a liquid and/or electrical power supply breakdown. This makes it possible to reliably inform a user of a liquid and/or electrical power supply breakdown of the system, while dispensing with the use of sensors and/or detectors in order to determine this breakdown.

According to a particular technical feature of the invention, the system also comprises a reservoir of disinfecting and/or degreasing liquid, the ring being integral with the reservoir, the absorbing pad being in fluid communication with the reservoir.

According to a particular technical feature of the invention, the ring and the reservoir form a single piece. The single piece is, for example, advantageously obtained via a manufacturing method by printing in three dimensions. This makes it possible to manufacture the ring with different sizes of reservoirs. The final user can thus advantageously select the volume of his/her reservoir. The base value of the latter is, for example, established at 10 ml, which allows an autonomy of approximately one week under standard utilization conditions. By varying the volume of the reservoir, the final user can, for example, double or even triple this volume.

According to a variant embodiment of the invention, a first opening is provided in the ring facing the absorbent pad, said opening leading into the reservoir, the reservoir and the opening being configured so that the liquid flows to the pad, through the opening, when the lever is inclined downward. The variant embodiment allows the pad to be recharged by sprinkling, due to the effect of gravity, each time the handle is actuated. This method of recharging the pad corresponds to the case of utilization where the handle is used in a sustained manner, for example in daily and/or diurnal use of the handle.

According to a variant or an additional embodiment of the invention, a second opening is provided in the ring facing the absorbent pad, said opening leading into the reservoir and the system also includes a capillary wick arranged through the opening into the reservoir, and in contact with the absorbent pad, to allow a transfer of liquid by capillary effect from the reservoir to the absorbent pad. This variant or this additional embodiment allows the pad to be recharged by capillary effect. This recharging method corresponds to a utilization case where the handle is slightly used and/or the pad is not fed by sprinkling, for example in infrequent and/or nocturnal use of the handle.

To this end, the invention also relates to an assembly including at least one door handle equipped with an operating lever and with a lever support, the assembly also comprising a cleaning and/or disinfection system for a hollow tube as described above, the hollow tube constituting the lever.

Particular forms of the assembly are defined according to the invention.

Advantageously, the assembly also comprises a latching device for the door by action on the lever, said device including a shaft integral in rotation with a square half-turn bolt of the door, and three parts mounted around the shaft and each forming a pivoting connection with the shaft, a first part forming a first pivoting connection with the shaft; a second part being attached to the lever support and forming a second pivoting connection with the shaft, and a third part arranged between the first and second parts and forming a third pivoting connection with the shaft; the device also including a first system of stops between the first part and the second part, so as to constrain the first part in its angular travel; and a second system of stops between the third part on the one hand and the first part or the second part on the other hand; the latching device also including a system for transforming the pivoting movement of the third part into a pivoting movement on a square dead bolt of the door, for latching or unlatching the door.

Due to the device for latching the door by action on the lever, a user can latch and unlatch the door by only actuating the lever of the door handle. This allows the user to avoid touching a dedicated locking button, potentially dirty and infected because it has not been washed by the system according to the invention. This therefore avoids any risk for the user of potential contamination during latching or unlatching of the door. Thus, due to an invention of this type according to the invention, an integral barrier to bacterial transmission is advantageously obtained over the entire sequence of opening, closing, latching and unlatching the door.

According to a second aspect of the invention, complementary to but independent of the first aspect, the invention also relates to a device for latching the door by action on an operating lever of a door handle, the handle also comprising a lever support; the device including a shaft integral in rotation with a square half-turn bolt of the door, and three parts mounted around the shaft and forming a first pivoting connection with the shaft; a second part being attached to the lever support and forming a second pivoting connection with the shaft, and a third part arranged between the first and second parts and forming a third pivoting connection with the shaft; the device also comprising a first system of stops between the first part and the second part, so as to constrain the first part in its angular travel; and a second system of stops between the third part on the one hand and the first part or the second part on the other hand; the latching device also including a system for transforming the pivoting movement of the third part into a pivoting movement on a square dead bolt of the door, for latching or unlatching the door. This advantageous solution allows the user to avoid touching a dedicated locking button, potentially dirty and infected, and imposes no modification or additional element(s) on the door itself, or on the door frame.

Advantageously, the third part and the pivoting movement transformation system are configured so that a movement of the second part in a first direction of rotation causes a movement of the third part and of the pivoting movement transformation system, in order to lock the door, and that a movement of the second part in a second direction of rotation, opposite to the first direction, causes a movement of the first part and of the shaft, in order to open the door. This allows a user to be able to easily and intuitively open or close the door, by action only on the lever of the handle which acts on the second part via the lever support. For example, one possible embodiment consists in that the user can open the door via a downward movement of the lever which acts on the square half-turn bolt of the door; and can latch the door via an upward movement of the lever which acts on the square dead bolt of the door. Once the door is latched, the unlatching can be accomplished via a downward movement of the lever which acts on the second part, therefore on the first part via the first system of stops, and therefore on the third part due to the second system of stops.

Advantageously, the first pivoting connection is configured to be on the angular travel of the handle on the side of the door opposite the installation side of the latching device, so that an inclination of the lever on the side of the door opposite the installation side of the device, causing a rotation of the shaft, is decoupled from any movement on the first part. This makes it possible to prevent any unintentional unlatching of the door by action on the lever on the side opposite the installation side of the unlatching device. When the user has latched the door on his/her side, a third person can thus not unlatch the door by inclining the handle, particularly by inclining it downward.

BRIEF DESCRIPTION OF THE FIGURES

The goals, advantages and features of the cleaning and/or disinfecting system for a hollow tube according to the invention, as well as the assembly comprising it, will appear more clearly in the following description on the basis of at least one non-limiting form of execution illustrated by the drawings in which:

FIG. 1 is a perspective view of an assembly comprising a door handle as well as a cleaning and/or disinfecting system for a hollow tube constituting the lever of the handle, and a door latching device by action on the lever, according to the invention;

FIG. 2 is a perspective view of the cleaning and/or disinfecting system of FIG. 1, the system comprising a lever, a ring and a liquid reservoir;

FIG. 3 is a similar view to that of FIG. 2, showing the interior of the lever, and in particular the electromechanical actuation of the ring;

FIG. 4 is a view of the back of the system of FIG. 2, seen in a direction D1 of longitudinal extension of the lever;

FIG. 5 is a bottom view of the system of FIG. 2;

FIG. 6 is a perspective view of the electromechanical actuating device of FIG. 3;

FIG. 7 is a perspective view of the ring and the reservoir of FIG. 2;

FIG. 8 is a perspective view of the lever of FIG. 2;

FIG. 9 is a perspective view of the door latching device of FIG. 1, the device including an attachment support, a mechanical system and a gear assembly;

FIG. 10 is a view similar to that of FIG. 9, in which the attachment support has been concealed;

FIG. 11 is a perspective view of the mechanical system of FIG. 9, the mechanical system comprising a shaft and three parts mounted around the shaft;

FIG. 12 is a perspective view of the mechanical system of FIG. 10, in which one of the three parts has been concealed;

FIG. 13 is a perspective view of the shaft of FIG. 10;

FIG. 14 is a perspective view of a first part from FIG. 10;

FIG. 15 is a perspective view of a second part from FIG. 10; and

FIG. 16 is a perspective view of a third part from FIG. 10.

DETAILED DESCRIPTION OF THE INVENTION

FIG. 1 shows an assembly 1 including at least one door handle 2 equipped with a lever 4 for operating the handle and with a lever 4 support 6. The assembly 1 also includes at least one cleaning and/or disinfecting system 8 for a hollow tube 4 constituting the lever, and a door latching device 10 by action on the lever 4. As a variant, and although only a single handle 2 and a single system 8 are shown in FIG. 1 and in the following figures, the assembly 1 can also comprise two handles 2 and two cleaning and/or disinfecting systems 8, each system 8 being dedicated to the cleaning and/or the disinfection of one of the levers 4 connected to a respective handle 2. In this specific case, each handle 2 is arranged on a respective side of the door. Also as a variant, the system 8 is adapted to the cleaning and/or disinfection of any hollow tube 4, possibly being able to be a tube of a bar equipping a transportation means such as a bus or subway, a marshal's baton type handle or even a handrail such as, for example, a stairway handrail. Without this being limiting within the scope of the present invention, the hollow tube 4 has, for example, a diameter of between 30 mm and 50 mm.

The lever 4 has, for example, a cylindrical shape. The lever 4 extends in its greatest dimension in a longitudinal direction D1 and is equipped with a longitudinal slot 11 to allow the passage of a translation driving element, as will be detailed hereafter. A slot 11 of this type, which extends for example on the underside of the lever 4 for esthetic reasons, is visible in FIGS. 4 and 5. The length of the longitudinal slot 11, measured in the longitudinal direction D1, is for example between 80 mm and 130 mm. Moreover, according to a particular exemplary embodiment shown in FIG. 8, the lever 4 can also include a longitudinal cutout 12 allowing the introduction of an electromechanical actuation device 20 within the lever 4. Preferably, the lever 4 or the ring 18 is equipped with at least one visual marking, a visual marking of this type not being visible in the figures for reasons of clarity. A visual marking of this type takes, for example, the form of a colored marking on the outer surface of the lever 4 or on the upper face of the ring 18, or even an engraved locator on this outer surface or on this upper face and is indicative of a liquid and/or electric power supply breakdown. Without this being limiting in the case of the present invention, the lever 4 has for example a diameter of between 20 mm and 27 mm and a total length, measured in the longitudinal direction D1, of between 150 mm and 200 mm. The lever 4 consists, for example, of a metal alloy, for example stainless steel.

The lever support 6 is conventionally mounted movable in rotation relative to the door, and in particular relative to a support device fixed on it, such as for example the latching device 10 in the illustrative example of FIG. 1. As a variant (not shown), the support device can for example be a conventional door escutcheon. The angular travel of the support 6 is typically between 0 and 60 degrees, the travel being measured relative to a substantially horizontal direction when the assembly 1 is attached to a door. The support 6 is integral in rotation with a part, itself connected to a square half-turn bolt of the door, as will be detailed hereafter, to allow the opening or the closing of the door. In a particular exemplary embodiment visible in FIGS. 1 to 3, the support 6 consists of a single one-piece material part. This one-piece part comprises, for example, a first substantially tubular portion 13, and a second substantially parallelepiped portion 14. The lever 4 is partially received in the first tubular portion 13, and is attached to it, for example by means of one or more screws. The one-piece part constituting a support 6 is, for example, made of plastic or metallic material.

As illustrated in FIGS. 2 to 5, the cleaning and/or disinfection system 8 of the lever 4 comprises, in addition to the lever 4, a ring 18 enclosing an absorbent pad impregnated with a disinfecting and/or degreasing liquid, and an electromechanical actuating device 20 for the ring 18. The absorbent pad is not shown in the figures for reasons of clarity.

According to one particular embodiment, shown in FIGS. 1 to 5 and 7, the system 8 also comprises a disinfecting and/or degreasing liquid reservoir 16.

According to another embodiment, not shown in the figures, the system 8 does not include a disinfecting and/or degreasing liquid reservoir 16. In this embodiment, the absorbent pad is arranged around the lever 4, and surrounds the latter at least partially. The absorbent pad, which has for example a substantially circular or annular shape, is thus arranged between the lever 4 and the ring 18 and is integral with the ring 18. In this case, the ring 18 includes, for example, a first substantially annular portion, in which the pad is arranged, and a second portion in the form of a longitudinal tab extending along the direction D1 and equipped with a longitudinal slot allowing the insertion and the integration of a translation drive element 26. Preferably, the absorbent pad completely surrounds the lever 4, allowing the lever 4 to be cleaned over its entire circumference. The absorbent pad has high absorption capacities, for example by being capable of absorbing a quantity of liquid substantially equal to four times the weight of the empty pad. In order to recharge the system 8 with disinfecting and/or degreasing liquid, a user of the system 8 can thus directly impregnate the absorbent pad by means of an applicator bottle or a syringe, for example. This advantageously makes it possible to dispense with any recharging of a connected reservoir, and thus facilitates the operation of recharging with liquid. The absorbent pad is typically made of a textile material, such as for example synthetic polyester or natural wool baize. When the absorbent pad has an annular shape, the absorbent pad has for example an inside diameter of between 25 mm and 30 mm, an outside diameter of between 35 mm and 40 mm, and a length, measured along the longitudinal direction D1, of between 10 mm and 30 mm.

In the particular embodiment shown in FIGS. 1 to 5 and 7, the reservoir 16 is configured to contain a disinfecting and/or degreasing liquid. A liquid of this type is for example an alcohol-based liquid, or a hydrogen peroxide-based liquid integrating silver ions, without this being limiting within the scope of the present invention. A filling opening 21 is for example provided on an outside surface of the reservoir 16, in order to allow a user to fill the reservoir 16, for example by means of an applicator bottle (not shown).

The ring 18 is mounted so as to slide on the lever 4 along the longitudinal direction D1. The ring 18 is able to slide in the two translation orientations S1, S2 visible in FIGS. 1 and 2, along this direction D1. The ring 18 comprises for example a first portion with a substantially annular shape, and a second longitudinal portion. In this case, the lever 4 is arranged in the center of the annulus forming the first portion of the ring 18, as illustrated in FIGS. 1 and 2. In the particular embodiment shown in FIGS. 1 to 5 and 7, the ring 18 is integrated with the reservoir 16. More precisely, the second longitudinal portion of the ring 18 encloses the reservoir 16. According to a particular exemplary embodiment illustrated in particular in FIGS. 4 and 5, a longitudinal slot 23 is provided in the ring 18 to allow the insertion and integration of a translation drive element 26, as will be detailed hereafter. The slot 23 extends for example on the bottom of the second longitudinal portion of the ring 18, typically over a portion of its length. The length of the longitudinal slot 23, measured in the longitudinal direction D1, is for example between 20 mm and 25 mm.

Without this being limiting within the scope of the present invention, the first annular portion of the ring 18 has for example a diameter of between 35 mm and 50 mm and a length, measured along the longitudinal direction D1, of between 20 mm and 35 mm.

Preferably, as shown in the illustrative example of FIGS. 1 to 5 and 7, the reservoir 16 and the ring 18 form a single one-piece part. A one-piece part of this type is for example obtained via a manufacturing process by printing in three dimensions, also called 3D printing. The one-piece part constituting the reservoir 16 and the ring 18 is for example made from a plastic material. Preferably, the reservoir 16 has a capacity substantially equal to 10 mL, for example. However, other capacities can be contemplated for the reservoir 16, extending for example from 10 mL to 30 mL. In particular, due to the 3D printing method used for the manufacture of the reservoir 16 and of the ring 18, the final user can advantageously opt for the capacity of his/her choice for the reservoir 16, depending in particular on the autonomy constraints desired.

The absorbent pad is arranged around the lever 4 and surrounds the latter at least partially. The absorbent pad, which has for example a substantially circular or annular shape, is thus arranged between the lever 4 and the ring 18 and is integral with the ring 18. Preferably, the absorbent pad completely surrounds the lever 4, making it possible to clean the lever 4 over its entire circumference. When the system 8 comprises a reservoir 16, the absorbent pad is in fluid communication with the latter. More precisely, according to a preferred exemplary embodiment illustrated in FIG. 7, an opening 22A is provided in the ring 18 facing the absorbent pad. The opening 22A leads into the reservoir 16. The reservoir 16 and the opening 22A are configured so that liquid flows from the reservoir 16 to the pad, through the opening 22A, when the lever 4 is inclined downward. Due to the inclination of the lever 4 during its manipulation by a user, liquid contained in the reservoir 16 can leave the opening 22A by gravity and moisten the absorbent pad. This makes it possible to rapidly moisten the pad, for example after several seconds after the inclination of the lever 4, following a manipulation of the handle 2. This method of recharging the pad by sprinkling corresponds to a utilization case where the handle 2 is used in a sustained manner, for example during periods during peak hours, in daily and/or diurnal use of the handle 2.

As a variant or additionally, and as illustrated in FIG. 7, another opening 22B is provided in the ring 18 facing the absorbent pad. The opening 22B leads into the reservoir 16, and the system 8 also includes a capillary wick, a wick of this type not being shown in the figures for reasons of clarity. The capillary wick is arranged through the opening 22B into the reservoir 16, and is in contact with the absorbent pad, to allow a transfer of liquid by capillary action from the reservoir 16 to the absorbent pad. This makes it possible to guarantee that a pad has been impregnated with liquid without any need to manipulate the handle 2. This method for recharging the pad by capillary action corresponds to a utilization case where the handle is only used a little and/or the pad is not fed by sprinkling, for example during off-peak periods such as nocturnal periods. Even if no manipulation of the handle 2 has taken place for ten hours or so during the night, this recharging method by capillary action makes it possible to guarantee that the pad will be moist in the early morning.

Preferably, and as illustrated in FIG. 7, the pad is received in the ring 18 at a location 24, said location 24 being axially offset from the mechanical connection between the ring 18 and a translation drive element 26 provided on the electromechanical actuation element 20. This makes it possible to have the stroke of the actuating device 20 coincide with the stroke of the ring 18, and thus clean the full length of the lever while using all possible travel of the device 20. The absorbent pad can consist of any type of absorbing and/or capillary material. For example, and without this being limiting within the scope of the present invention, the absorbent pad can be made of textile material, such as for example synthetic polyester or natural wool baize.

As illustrated in FIGS. 3, 4 and 6, the electromechanical actuating device 20 is arranged inside the hollow tube constituting the lever 4 and comprises a longitudinal translation element 26. The element 26 is visible in FIGS. 4 and 6. Preferably, as illustrated in FIGS. 4 and 6, the device 20 also comprises a motor 28 supplied with electrical power, and a pulley/belt assembly 30 actuated by the motor 28. Still preferably, the device 20 also comprises a microcontroller for controlling the motor 28, connected to the motor 28; as well as an inclinometer connected to the microcontroller. Also preferably, the device 20 also comprises a chopper connected to the motor 28, the microcontroller and the power supply battery(ies). The microcontroller, inclinometer and chopper, which are not shown in the figures for reasons of clarity, appear typically in the form of electronic components connected to a printed circuit board 32.

As illustrated in FIG. 4, the longitudinal translation drive element 26 protrudes through the longitudinal slot 11 of the lever 4 and is mechanically connected to the ring 18. To this end, and according to the particular exemplary embodiment illustrated in FIGS. 1 to 6, the longitudinal translation element 26 is for example inserted through the longitudinal slot 23, in order to allow mechanical connection with the ring 18. Thus, the element 26 is configured to allow the movement of the ring 18 in longitudinal translation along the lever 4, more precisely along the longitudinal direction D1. According to this particular exemplary embodiment, the element 26, which is typically a movable carriage equipped with a tab 34, is also connected to the pulley/belt assembly 30, as illustrated in FIG. 6. The tab 34 protrudes through the respective longitudinal slots 11, 23 of the lever 4 and the ring 18, and allows the driving in longitudinal translation of the ring 18 along the lever 4, the longitudinal slot 23 of the ring 18 being shorter than the longitudinal slot 11 of the lever 4. As illustrated in FIG. 6, the tab 34 has for example a "T" shape.

The electromechanical actuating device 20 is a motorized linear potentiometer. In case the longitudinal translation drive element 26 is a movable carriage, the movable carriage 26 is mounted in translation on a fixed portion 36 of the potentiometer. A linear potentiometer of this type comprises an electrically resistant track and a cursor movable along the track. In the case where the longitudinal translation drive element 26 is a movable carriage, the tab 34 of the movable carriage 26 forms the cursor. The resistant track is terminated at each of its ends by two terminals, one of the two terminals being connected to a high electrical potential, the other terminal being connected to a low electrical potential. A third terminal is connected to the cursor 34. Thus, the value of the resistance measured between the third terminal and one of the two other terminals varies in proportion to the distance between the end terminals of the track and the cursor 34. This makes it possible to obtain an advantageous potentiometric feedback within the scope of the present invention, because it allows precise information to be obtained regarding the position of the cursor 34 and therefore of the ring 18. This makes it possible in particular to guarantee that the movement of the ring 18, and therefore the cleaning of the lever 4, has actually occurred over the entire length of the lever 4. The motorized linear potentiometer 20 has a stroke substantially equal to 100 mm. Without this being limiting within the scope of the present invention, the motorized linear potentiometer 20 shown in FIGS. 4 and 6 is a potentiometer of the Alps® brand known as model 401840 (protected brand and model).

The motor 28 is for example supplied with electrical power via one or more batteries (not shown in the figures for reasons of clarity). The battery(ies) can be rechargeable or non-rechargeable batteries. The use of rechargeable batteries, which can for example be recharged via a USB (Universal Serial Bus) type cable, allows a virtuous economic and ecological balance to be offered. Typically, rechargeable batteries of this type can be selected from among polymer lithium ion Li—Po (from Lithium Polymer), or nickel-metal hydride NiMH. Li—Po batteries have high capacity but require a battery compartment that is fireproof and implosion-resistant to be provided in the system 8. NiMH batteries have increased safety in use but require the use of an external charger. Preferably, the supply voltage supplied by the battery(ies), rechargeable or not, is substantially equal to 9 V. In the case of non-rechargeable batteries, the latter are for example selected so as to store energy of between substantially 0.4 Ah and 0.6 Ah. This leads to a lifetime substantially equal to 4,000 cleaning cycles which, applied to an establishment receiving the public, establishes the lifetime at approximately 3 months, under forced usage conditions. In the case of rechargeable batteries, the estimated lifetime is substantially equal to 3,500 cleaning cycles. The motor 28 is typically a direct current brush motor, without this being limiting within the scope of the present invention.

The pulley/belt assembly 30 is driven by the motor 28, and is configured to move in translation, along the longitudinal direction D1, the longitudinal translation drive element 26.

According to a preferred exemplary embodiment, the microcontroller comprises processing means and memory means storing a source code, the source code including program instructions which, when executed by the processing means, trigger a control sequence of the motor in order to move the ring 18 in longitudinal translation along the lever 4. Preferably, the microcontroller also comprises a precalibrated counter.

Preferably, a phase of acceleration at the start and deceleration upon arrival of the ring 18 is implemented in the program instructions of the source code. This makes it possible to avoid in the system 8 any noise inherent in "water hammers" connected with the end-of-stroke of the ring 18. Preferably too, the microcontroller is configured so as to make it possible to select and/or configure a desired cleaning strategy. More precisely, the cleaning strategy, selected and/or configured via the source code, can allow the parameters, such as for example the movement speed, the movement frequency, and/or the values of acceleration and of deceleration of the ring 18 to be modified at the beginning and at the end of the movement. The source code of the system 8 can thus, for example, be configured so that the system 8 cleans and/or disinfects the lever 4 with a given frequency even if the lever 4 has not been used.

Still preferably, the source code is configured so that the system 8, in particular the electromechanical actuating device 20, repositions the ring 18 to its starting position when it comes into contact with the hand of a person. A system of anti-pinch feedback of this type is for example made possible by a comparison, performed by the microcontroller, of the measured position of the ring 18, a position measurement of this type being obtained via the potentiometric feedback offered by the potentiometer 20. Advantageously, the source code can for example be configured so that the ring 18 returns to its starting position at an accelerated speed, corresponding to a duration of 1 second instead of 2 seconds in normal operation, in order to limit the inconvenience caused by the presence of the ring 18 to the final user.

The precalibrated counter records a predetermined number of cycles of the system 8 corresponding to a liquid and/or electrical power supply breakdown. The predetermined number of cycles is for example determined by prior calibration studies. Preferably, the control sequence of the motor 28 is configured within the source code so that, when the counter has reached the predetermined number of cycles, the microcontroller commands the motor 28 to bring the ring 18, at the end of its movement, to a predetermined position on the lever 4 allowing the visual marking to appear, either on the lever 4 directly or on top of the ring 18. This makes it possible to reliably notify maintenance personnel regarding the need to recharge the liquid and/or the electrical power supply, or the need to replace the power supply batteries when they are not rechargeable. In addition, a solution of this type makes it possible to dispense with the use of sensors and/or detectors in order to determine the liquid and/or electrical power supply breakdown.

The motor control microcontroller 28 is advantageously configured to allow effective management of liquid and/or electrical power supply autonomy of the system, as well as selection by the user of the desired cleaning conditions and/or strategy. The microcontroller appears for example in the form of an electronic chip connected on the printed circuit board 32. The microcontroller is for example selected so as to have a very low energy consumption in sleep mode, in the range of a few nanoamperes, typically an energy consumption substantially equal to 50 nA. This makes it possible to increase the lifetime of the power supply batteries.

The inclinometer is configured to detect a movement of the lever 4, typically a return movement of the lever 4 to its initial horizontal position. As a variant, the movement of the lever 4 detected by the inclinometer can be a downward movement, corresponding to an opening of the door. The inclinometer is also configured to transmit to the microcontroller a corresponding detection signal. The inclinometer consists for example of a tube comprising a ball able to move in the tube, as well as a contact switch. The ball is made of an electrically conducting material and is able to move inside the tube when the handle 2 is actuated. The switch is connected to the microcontroller so as to be able to transmit to it the detection signal when the switch is closed by contact with the ball. This interruption at the level of the microcontroller awakens the latter. After a predefined duration has elapsed since the reception of the detection signal, the microcontroller is configured to transmit to the motor 28, via the chopper, a signal for controlling a back-and-forth movement of the ring 18 along the lever 4. The microcontroller then returns to its sleep mode. The predefined duration is, for example, between one second and three seconds. The microcontroller is, for example, configured so that the control of a back-and-forth movement of the ring 18 corresponds to an actual back-and-forth movement with a duration lasting typically between one second and four seconds. A duration of this type allows the correct application of the liquid over the entire surface and the entire length of the lever 4.

The chopper is adapted to control the motor 28. The chopper is selected for example so as to have a very low energy consumption in sleep mode, typically an energy consumption substantially equal to 80 nA. This allows the lifetime of the power supply batteries to be increased.

FIGS. 9 and 10 show a door latching device 10 by action on a door handle 2 operating lever 4, advantageously integrated for example within the assembly 1 of FIG. 1. As a variant, the latching device 10 can equip any door handle 2 equipped with an operating lever 4 and with a lever support 6, and not necessarily equipped with the cleaning and/or disinfection system 8.

The latching device 10 includes a shaft 40; three parts 42A, 42B, 42C mounted around the shaft 40 and each forming a pivoting connection with the shaft 40; and a system 44 for transforming the pivoting movement of one of the parts 42C into a pivoting movement on a square dead bolt of the door. A square dead bolt of this type is not shown in the figures for reasons of clarity. The system for transforming the pivoting movement 44 allows, under the influence of a rotation movement of the part 42C, the latching or unlatching of the door. Preferably, as illustrated in FIG. 9, the latching device 10 also includes an attachment support 46 intended to be attached to the door.

The shaft 40 is integral in rotation with a square half-turn bolt of the door, a square half-turn bolt of this type not being shown in the figures for reasons of clarity. As can be seen in FIGS. 9 to 13, the shaft 40 is pierced, along its main direction of extension D2, with an opening 48 for receiving the square half-turn bolt. For the rest of the description, the main extension direction D2 of the shaft 40 will be called the longitudinal direction, and any direction perpendicular to the longitudinal direction D2 will be called a transverse direction. The opening 48 has a shape complementary to that of the square half-turn bolt in order to ensure integration in rotation, for example a substantially rectangular or square shape in the illustrative example of these figures.

In the particular exemplary embodiment shown in FIGS. 9 to 13, the shaft 40 is equipped, on its outer surface, with at least one transverse slot 50. Preferably, the shaft 40 comprises two transverse slots 50 located at substantially 180 degrees from one another on the outer surface of the shaft 40.

A first part 42A forms a first pivoting connection 52A with the shaft 40. To this end, in a particular exemplary embodiment shown in FIGS. 13 and 14, the first part 42A has a substantially annular shape and has at least one transverse stop 54 protruding on an inner perimeter of the annulus. Preferably, as can be seen in FIG. 14, the first part 42A comprises two transverse stops 54, located at substantially 180 degrees from one another on the inner perimeter of the annulus formed by the first part 42A. The empty central portion of the annulus allows the passage of the shaft 40. Each transverse stop 54 is thus inserted into one of the transverse slots 50 of the shaft 40. Under the influence of the rotation of the first part 42A round the shaft 40, each transverse stop 54 is able to move in a corresponding transverse slot 50 to a support position on an inner edge 56 of the shaft 40, making it possible to drive the shaft 40 and therefore the half-turn bolt in rotation. As a variant, not shown, the slot(s) 50 provided on the shaft 40 can be replaced by stops, and the transverse stop(s) 54 provided on the first part 42A can be replaced by openings complementary to the stops provided on the shaft 40.

In a preferred embodiment shown in FIGS. 9 to 14, the first pivoting connection 52A is configured to be on the angular travel of the handle 2 on the side of the door opposite the installation side of the latching device 10. Thus, an inclination of the lever 4 on the side of the door opposite the installation side of the device 10, causing a rotation of the shaft 40, is decoupled from any movement on the first part 42A. To this end, in the particular exemplary embodiment shown in FIGS. 13 and 14, each transverse slot 50 is configured in such a manner that an inclination of the lever 4 on the side of the door opposite the installation side of the latching device 10, causing a rotation of the shaft 40, is decoupled from any movement on the corresponding stop 54 of the first part 42A. This decoupling has as its consequence that in the latching position of the device (obtained for example as a result of the actuation of the lever 4 by a user inside a room such as a toilet or rest room), a third person who inclines the handle 2 on the outside causes the square half-turn bolt of the door, and therefore the shaft 40, to pivot, but without driving the transverse stops 54 of the first part 42A in rotation, and therefore without acting on the third part 42C connected to the latching and unlatching of the door. This allows any unintentional unlatching of the door by action on the lever 4 on the side opposite the installation side of the device 10 to be prevented. When a user has latched the door on his/her side by action on the lever 4, a third person can thus not unlatch the door by inclining the handle 2, particularly by inclining it downward. In order to satisfy current safety standards, it is often possible for him/her to unlatch the system on an emergency basis in the same manner as the current standards, namely by means of a coin or a screwdriver.

A second part 42B forms a second pivoting connection 52B with the shaft 40. When the latching device 10 is integrated within the assembly 1 of FIG. 1, the second part 42B is attached to the support 6 of the lever 4, for example by means of screws (not shown). The second part 42B is visible in detail in FIGS. 11 and 16. According to this exemplary embodiment, the second part 42B has a substantially flat shape and is hollowed at its center 58 to allow the passage of the shaft 40. The latching device 10 also includes a system of stops 60, 62 between the first part 42A and the second part 42B, so as to constrain the first part 42A in its angular travel. More precisely, according to a particular exemplary embodiment shown in FIGS. 11 and 16, the second part 42B is equipped with a longitudinal lug 60 which extends parallel to the longitudinal direction D2, from a surface of the second part 42B opposite the surface of attachment to the lever support 6. According to this particular exemplary embodiment, the first part 42A is equipped on its outer perimeter with a transverse lug 62 in abutment against the longitudinal lug 60 of the second part 42B. A transverse lug 62 of this type is visible in FIGS. 11 and 14. Consequently, when a user pivots the handle 2 in the clockwise direction S3, the handle 2 attached to the second part 42B by means of the support 6 pivots the first part 42A in the clockwise direction S3 by means of the longitudinal lug 60 which acts on the transverse lug 62. The first part 42A then pivots the shaft 40 by means of stops 54 which slide in the slots 50 and cooperate with an inner edge 56 of the shaft 40, causing the rotation of the shaft 40 in the clockwise direction S3. The shaft 40 then drives with it the square half-turn bolt of the door, causing the withdrawal of the half-turn bolt from its recess in the door and therefore its opening.

A third part 42C forms a third pivoting connection 52C with the shaft 40. The third part 42C is arranged between the first and second parts 42A, 42B, and is also mechanically connected to the pivoting movement transformation system 44. The third part 42C is visible in detail in FIGS. 11, 12 and 15. The latching device 10 also includes a system of stops 60, 64, 66, 68A, 68B between the third part 42C on the one hand and the first part 42A or the second part 42B on the other hand. More precisely, according to the exemplary embodiment of FIGS. 11, 12 and 15, the third part 42C is hollowed at its center 70 to allow the passage of the shaft 40. The third part 42C is equipped with a toothed peripheral portion 72 engaged with the pivoting movement transformation system 44, with a peripheral portion forming a support stop 64, and a peripheral portion 66 having a notch 78 to allow the passage of the longitudinal lug 60 of the second part 42B. The peripheral portion forming a support stop 64 is thicker than two other peripheral portions 72, 66, the thickness being considered to be the dimension which extends in the longitudinal direction D2. According to this particular exemplary embodiment, the first part 42A is equipped on its outer perimeter with two transverse lugs 68A, 68B. These two transverse lugs 68A, 68B are visible in FIGS. 12 and 14. A first transverse lug 68A is in abutment against the peripheral portion forming a support stop 64, and forms a stop of the third part 42C relative to the first part 42A. A second transverse stop 68B is located on the other side of the peripheral portion forming a support stop 64, relative to the first transverse lug 68A, and is able to press on this peripheral portion 64 during a rotation of the first part 42A in the clockwise direction S3, and thus drive the third part 42C in rotation in the direction S3.

The longitudinal lug 60 is in abutment against the peripheral portion 66, as illustrated in FIG. 11. In this manner, a rotation movement of the second part 42B in the counter-clockwise direction S4 causes a rotation of the third part 42C in the same direction of rotation S4 and therefore, via the action of the toothed peripheral portion 72, a movement of the pivoting movement transformation system 44 in order to latch the door. More precisely, and as illustrated in FIGS. 10 and 11, when a user pivots the handle 2 in the counter-clockwise direction S4, the handle 2 attached to the second part 42B by means of the support 6 pivots the third part 42C in the counter-clockwise direction S4 by means of the longitudinal lug 60 which acts on the peripheral portion 66. The third part 42C then drives, via the toothed peripheral portion 72, a movement of the pivoting movement transformation system 44 which acts on the square dead bolt in order to latch the door. Once in the latching position of the device 10 and therefore of the door, the user can then unlatch it by pivoting the handle 2 in the clockwise direction S3. More precisely, in the latching position of the device 10, when the user pivots the handle 2 in the clockwise direction S3, the handle 2 attached to the second part 42B by means of the support 6 pivots the first part 42A in the clockwise direction S3 by means of the longitudinal lug 60 which acts on the transverse lug 62. This leads to the withdrawal of the half-turn bolt from its recess, via the rotation of the shaft 40, as previously indicated. In addition, and as illustrated in FIG. 12, this rotation of the first part 42A in the clockwise direction S3 causes a rotation of the second part 42C in the same direction S3, via the action of the second transverse lug 68B on the peripheral portion forming a support stop 64. The third part 42C then drives, via the toothed peripheral portion 72, a movement of the pivoting movement transformation system 44 which acts on the square dead bolt in order to unlatch the door. The third part 42C then returns to its initial position, corresponding to a door unlatching position.

As illustrated in FIGS. 9 and 10, the pivoting movement transformation system 44 is for example a gear assembly, without this being limiting within the scope of the present invention. The pivoting movement transformation system 44 comprises for example a first toothed wheel 80 engaged with the toothed peripheral portion 72 of the third part 42C, and a second toothed wheel 82 integral in rotation with the square dead bolt of the door. The square dead bolt of the door acts on the latching or the unlatching of the latter. The pivoting movement transformation system 44 is for example configured to transform, via the toothed wheels 80, 82, an angular movement of 45 degrees on the third part 42C into a corresponding angular movement of 90 degrees on the square dead bolt.

The invention claimed is:

1. A cleaning and/or disinfection system (8) of a hollow tube (4), comprising:
   the hollow tube (4);
   a ring (18) mounted so as to slide over the hollow tube (4), the ring (18) enclosing an absorbent pad impregnated with a disinfecting and/or degreasing liquid, the absorbent pad being arranged around the hollow tube (4);
   an electromechanical actuating device (20) of the ring (18) arranged inside the hollow tube (4), said device (20) including a longitudinal translational drive element (26), wherein the electromechanical actuating device (20) is a motorized linear potentiometer;
   a longitudinal slot (11) is provided in the hollow tube (4), the longitudinal translational drive element (26) protruding through said longitudinal slot (11) and being mechanically connected to the ring (18), in order to move the ring (18) in longitudinal translation along the hollow tube (4);
   characterized in that the hollow tube (4) is a lever for operating a door handle (2);
   the system (8) also comprises a reservoir (16) of liquid disinfectant and/or degreaser, the ring (18) being integral with the reservoir (16), and the absorbent pad being in fluid communication with the reservoir (16);
   the ring (18) and the reservoir (16) form a single piece; and
   a first opening (22A) is provided in the ring (18) facing the absorbent pad, said opening (22A) leading into the reservoir (16), the reservoir (16) and the first opening (22A) being configured so that liquid flows from the reservoir (16) to the absorbent pad through the first opening (22A), when the lever is inclined downward.

2. The system (8) according to claim 1, characterized in that the electromechanical actuating device (20) also comprises a motor (28) fed electrically and a pulley/belt assembly (30) actuated by the motor (28), the longitudinal translational drive element (26) being connected to the pulley/belt assembly (30).

3. The system (8) according to claim 1, characterized in that the longitudinal translational drive element (26) is a movable carriage mounted so as to translate over a fixed portion (36) of the motorized linear potentiometer and including a tab (34), and in that a longitudinal slot (23) is provided in the ring (18), the tab (34) protruding though the respective longitudinal slots (11, 23) of the hollow tube (4) and of the ring (18).

4. The system (8) according to claim 1, characterized in that the hollow tube (4) or the ring (18) is equipped with at least one visual marking, the at least one visual marking comprising at least one colored marking or at least one engraved locator, said at least one visual marking being indicative of a liquid and/or electrical power supply breakdown.

5. The system (8) according to claim 1, characterized in that the electromechanical actuating device (20) also includes a motor control microcontroller connected to a motor (28).

6. The system (8) according to claim 5, characterized in that the electromechanical actuating device (20) also includes an inclinometer connected to the microcontroller, said inclinometer being configured to detect a movement of the lever (4) and to transmit to the microcontroller a corresponding detection signal, the microcontroller being configured to transmit to the motor (28), upon completion of a predefined period since the reception of the detection signal, a signal controlling a back-and-forth movement of the ring (18) along the lever (4).

7. The system (8) according to claim 5, characterized in that the microcontroller comprises a processor and a memory storing a source code, the source code including program instructions which, when executed by the processor, trigger a command sequence of the motor (28) for moving the ring (18) in longitudinal translation along the hollow tube (4).

8. The system (8) according to claim 7, characterized in that the microcontroller also comprises a precalibrated counter, the counter recording a predetermined number of cycles of the system (8), corresponding to a liquid and/or electrical power supply breakdown, and in that the command sequence of the motor (28) is configured within the source code so that, when the counter has reached the predetermined number of cycles, the microcontroller commands the motor (28) to bring the ring (18), at the end of its movement, to a predefined position on the hollow tube (4) allowing a visual marking to appear.

9. The system (8) according to claim 1, characterized in that a second opening (22B) is provided in the ring (18) facing the absorbent pad, said second opening (22B) leading into the reservoir (16), and in that the system (8) also includes a capillary wick arranged through the second opening (22B) into the reservoir (16) and in contact with the absorbent pad, to allow a transfer of liquid by capillary action from the reservoir (16) to the absorbent pad.

10. An assembly (1) comprising:
    the cleaning and/or disinfection system (8) for the hollow tube (4) according to claim 1; and
    a support (6) of the lever,
    wherein the door handle (2) is equipped with the lever.

11. The assembly (1) according to claim 10, characterized in that it also comprises a device (10) for latching the door by action on the lever (4), said device (10) including an axis (40) integral in rotation with a square half-turn bolt of the door, and three parts (42A, 42B, 42C) mounted around the shaft (40) each forming a pivoting connection (52A, 52B, 52C) with the shaft (40), a first part (42A) forming a first pivoting connection (52A) with the shaft (40); a second part (42B) being fixed to the support (6) of the lever (4) and forming a second pivoting connection (52B) with the shaft (40), and a third part (42C) arranged between the first and second parts (42A, 42B) and forming a third pivoting connection (52C) with the shaft (40); the device (10) also including a first system of stops (60, 62) between the first part (42A) and the second part (42B), so as to constrain the first part (42A) in its angular travel; and a second system of stops (60, 64, 66, 68B) between the third part (42C) on the one hand and the first part (42A) or the second part (42B) on the other hand; the latching device (10) also including a system (44) for transforming the movement of the third part (42C) into a pivoting movement on a square dead bolt of the door, for latching or unlatching the door.

12. The assembly (1) according to claim 11, characterized in that the third part (42C) and the pivoting movement transformation system (44) are configured so that a movement of the second part (42B) in a first direction of rotation (S4) causes a movement of the third part (42C) and the pivoting movement transformation system (44) in order to latch the door, and so that a movement of the second part (42B) in a second direction of rotation (S3) opposite to the first direction (S4) causes a movement of the first part (42A) and of the shaft (40), in order to open the door.

13. The assembly (1) according to claim 11, characterized in that the first pivoting connection (52A) is configured to be on the angular travel of the handle on the side of the door opposite to the installation side of the latching device (10), so that an inclination of the lever (4) on the side of the door opposite the installation side of the device (10), causing a rotation of the shaft (40), is decoupled from any movement on the first part (42A).

* * * * *